US00PP20785P2

(12) United States Plant Patent
Pryor

(10) Patent No.: US PP20,785 P2
(45) Date of Patent: Feb. 23, 2010

(54) ***PTILOTUS* PLANT NAMED 'PLATINUM WALLABY'**

(50) Latin Name: *Ptilotus exaltatus*
Varietal Denomination: Platinum Wallaby

(75) Inventor: Suzanne Kathleen Pryor, Berambing (AU)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 12/291,393

(22) Filed: Nov. 7, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell
(74) *Attorney, Agent, or Firm*—C. A. Whealy

(57) ABSTRACT

A new and distinct cultivar of *Ptilotus* plant named 'Platinum Wallaby', characterized by its compact, upright and mounded plant habit; freely basal-branching habit; small leaves; freely flowering habit; and silvery purple-colored flowers.

1 Drawing Sheet

Botanical designation: *Ptilotus exaltatus*.
Cultivar denomination: 'Platinum Wallaby'.

BACKGROUND OF THE INVENTION

The present invention relates to a new and distinct cultivar of *Ptilotus* plant, botanically known as *Ptilotus exaltatus* and hereinafter referred to by the name 'Platinum Wallaby'.

The new *Ptilotus* plant is a product of a planned breeding program conducted by the Inventor in Berambing, New South Wales, Australia. The objective of the breeding program is to create new compact and freely basal-branching Ptilotus cultivars with strong stems and numerous attractive flowers.

The new *Ptilotus* plant originated from a cross-pollination made by the Inventor in Berambing, New South Wales, Australia on Feb. 2, 2006, of two unnamed proprietary selections of *Ptilotus exaltatus*, not patented. The new *Ptilotus* was discovered and selected by the Inventor as a single flowering plant from within the progeny of the stated cross-pollination in a controlled greenhouse environment in Berambing, New South Wales, Australia on Oct. 1, 2006.

Asexual reproduction of the new *Ptilotus* plant by tissue culture in Tumbi Umbi, New South Wales, Australia since Dec. 1, 2007, has shown that the unique features of this new Ptilotus plant are stable and reproduced true to type in successive generations.

SUMMARY OF THE INVENTION

Plants of the new *Ptilotus* have not been observed under all possible environmental conditions. The phenotype may vary somewhat with variations in environment such as temperature and light intensity without, however, any variance in genotype.

The following traits have been repeatedly observed and are determined to be the unique characteristics of 'Platinum Wallaby'. These characteristics in combination distinguish 'Platinum Wallaby' as a new and distinct cultivar of *Ptilotus:*

1. Compact, upright and mounded plant habit.
2. Freely basal-branching habit.
3. Small leaves.
4. Freely flowering habit.
5. Silvery purple-colored flowers.

Plants of the new *Ptilotus* can be compared to plants of the female parent selection. Plants of the new *Ptilotus* differ from plants of the female parent selection in the following characteristics:

1. Plants of the new *Ptilotus* are more compact than plants of the female parent selection.
2. Plants of the new *Ptilotus* are more freely basally-branching than plants of the female parent selection.
3. Plants of the new *Ptilotus* are more tolerant to pathogens than plants of the female parent selection.

Plants of the new *Ptilotus* can be compared to plants of the male parent selection. Plants of the new *Ptilotus* differ from plants of the male parent selection in the following characteristics:

1. Plants of the new *Ptilotus* are more compact than plants of the male parent selection.
2. Plants of the new *Ptilotus* are more tolerant to pathogens than plants of the male parent selection.

Plants of the new *Ptilotus* can also be compared to plants of *Ptilotus splendens* 'Joey', not patented. Plants of the new *Ptilotus* differ from plants of 'Joey' in the following characteristics:

1. Plants of the new *Ptilotus* are more compact than plants of 'Joey'.
2. Plants of the new *Ptilotus* are more freely basally-branching than plants of 'Joey'.
3. Plants of the new *Ptilotus* have narrower leaves than plants of 'Joey'.
4. Plants of the new *Ptilotus* have longer and more pointed inflorescences than plants of 'Joey'.

BRIEF DESCRIPTION OF THE PHOTOGRAPHS

The accompanying colored photographs illustrate the overall appearance of the new *Ptilotus* plant, showing the colors as true as it is reasonably possible to obtain in colored reproductions of this type. Colors in the photographs may differ slightly from the color values cited in the detailed botanical description which accurately describe the actual colors of the new *Ptilotus* plant.

The photograph at the bottom of the sheet comprises a side perspective view of a typical flowering plant of 'Platinum Wallaby' grown in a container.

The photograph at the top of the sheet is a close-up view of typical inflorescences of 'Platinum Wallaby'.

DETAILED BOTANICAL DESCRIPTION

The aforementioned photographs and following observations, measurements and values describe plants grown in Bonsall, Calif., under commercial practice during the summer in a polyethylene-covered greenhouse. During the production of the plants, day temperatures ranged from 21° C. to 27° C. and night temperatures ranged from 18° C. to 21° C. Plants had been growing for four months when the description and photographs were taken. In the following description, color references are made to The Royal Horticultural Society Colour Chart, 2001 Edition, except where general terms of ordinary dictionary significance are used.

Botanical classification: *Ptilotus exaltatus* 'Platinum Wallaby'.

Parentage:

*Female, or seed, parent.*—Unnamed proprietary selection of *Ptilotus exaltatus*, not patented.

*Male, or pollen, parent.*—Unnamed proprietary selection of *Ptilotus exaltatus*, not patented.

Propagation:

*Type.*—By tissue culture.

*Time to initiate roots, summer.*—About ten days at 22° C.

*Time to initiate roots, winter.*—About two weeks at 15° C.

*Time to produce a rooted young plant, summer.*—About 15 to 20 days at 22° C.

*Time to produce a rooted young plant, winter.*—About 20 to 25 days at 18° C.

*Root description.*—Medium to thin in thickness, fibrous; white in color.

*Rooting habit.*—Moderate branching; sparse.

Plant description:

*Plant habit.*—Compact, upright and mounding.

*Growth habit.*—Vigorous.

*Plant height.*—About 43 cm.

*Plant diameter.*—About 46 cm.

*Lateral branch description.*—Branching habit: Freely basal-branching with about ten basal branches per plant. Length: About 35 cm. Diameter: About 4 mm. Internode length: About 2.7 cm. Strength: Strong. Texture: Smooth, glabrous; longitudinally ridged. Color: Close to 148A.

Foliage description:

*Arrangement.*—Alternate, simple.

*Length.*—About 5.2 cm.

*Width.*—About 1.2 cm.

*Shape.*—Oblanceolate to elongated spatulate.

*Apex.*—Acute.

*Base.*—Attenuate.

*Margin.*—Entire.

*Texture, upper and lower surfaces.*—Scattered pubescence.

*Venation pattern.*—Pinnate.

*Color.*—Developing leaves, upper and lower surfaces: Close to 148A. Fully expanded leaves, upper surface: Close to 137B; venation, close to 147C. Fully expanded leaves, lower surface: Close to 147B; venation, close to 147C.

*Petioles.*—Length: About 3 mm. Diameter: About 2 mm. Texture, upper surface: Pubescent; leathery. Texture, lower surface: Smooth, glabrous. Color, upper surface: Close to 148D. Color, lower surface: Close to 147D.

Flower description:

*Flower type and habit.*—Single star-shaped sessile flowers arranged in terminal and axillary spikes; spikes narrowly conical in shape. Inflorescences mostly upright with flowers initially facing upright to outwardly with development. Freely flowering habit, about 280 open flowers and flower buds developing per inflorescence.

*Natural flowering season.*—Long flowering period; plants flower from spring until autumn in California; flowering continuous during this period. Plants initiate flower development about four weeks after planting.

*Inflorescence longevity on the plant.*—About two months; flowers not persistent.

*Fragrance.*—Not detected.

*Inflorescence height.*—About 17 cm.

*Inflorescence diameter* (*at the base*).—About 4.5 cm.

*Flowers.*—Appearance: Flowers star-shaped with five lanceolate petals in a single whorl and are fused at the base. Diameter, at apex: About 2.2 cm. Diameter, at base: About 2.5 mm. Depth (length): About 2.7 cm.

*Flower buds.*—Length: About 2.5 cm. Diameter: About 4 mm. Shape: Lanceolate. Color: Close to 198B; towards the apex, close to N74B.

*Petals.*—Length: About 2 cm. Width: About 1 mm to 1.5 mm. Shape: Lanceolate. Apex: Acuminate. Margin: Entire. Texture, upper and lower surfaces: Pubescent. Color: When opening, upper surface: Close to 198C. When opening, lower surface: Close to N78B; pubescence, close to 202D. Fully opened, upper surface: Close to 198D; towards the margins and apices, close to N78B to N78C; color does not fade with development. Fully opened, lower surface: Close to N78C; pubescence, 198D; towards the apices, close to N78; color does not fade with development.

*Sepals.*—Arrangement: Three in a single whorl. Length: About 8 mm to 10 mm. Width: About 4 mm to 5 mm. Shape: Elliptical. Apex: Acuminate. Base: Truncate. Margin: Entire. Texture, upper and lower surfaces: Pubescent. Color, upper and lower surfaces: Close to 200C to 200D.

*Peduncles.*—Length: About 7.4 cm to 9.5 cm. Diameter: About 2.5 mm. Texture: Pubescent. Strength: Strong. Color: Close to 146B tinted with close to N78B.

*Reproductive organs.*—Stamens: Quantity per flower: Typically three. Filament length: About 1.6 mm. Filament color: Close to N74A. Anther shape: Crescent-shaped. Anther size: About 1 mm by 2 mm. Anther color: Close to 72C. Pollen amount: Scarce. Pollen color: Close to 165C. Pistils: Quantity per flower: Typically one. Pistil length: About 1.9 cm. Stigma shape: Rounded. Stigma color: Close to 70D. Style length: About 2.1 cm. Style color: Close to 157D. Ovary color: Close to 194B.

*Seed/fruit.*—Seed and fruit production has not been observed.

Disease/pest resistance: Plants of the new *Ptilotus* have been noted to be relatively tolerant to *Pythium* and *Phytoph-*

*thora*. Plants of the new *Ptilotus* have not been noted to be resistant to pests and other pathogens common to *Ptilotus*.

Temperature tolerance: Plants of the new *Ptilotus* have been observed to tolerate temperatures from about −5° C. to about 45° C.

It is claimed:

1. A new and distinct *Ptilotus* plant named 'Platinum Wallaby' as illustrated and described.

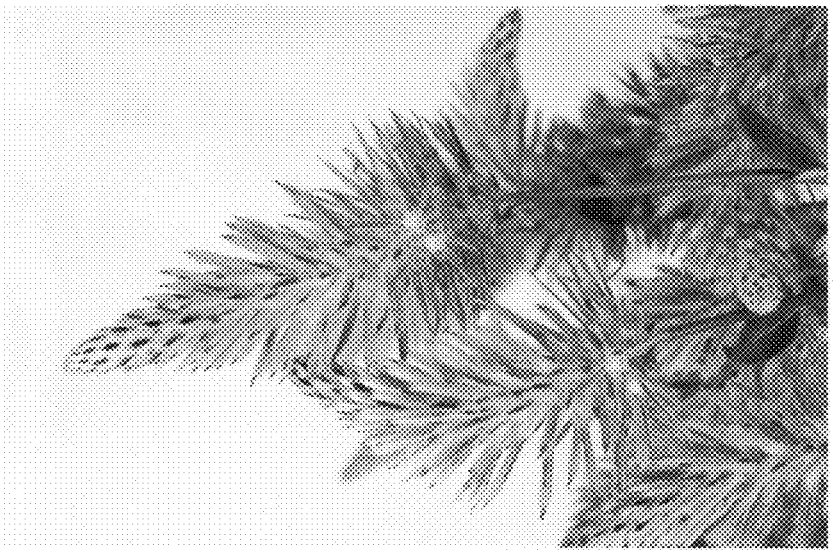
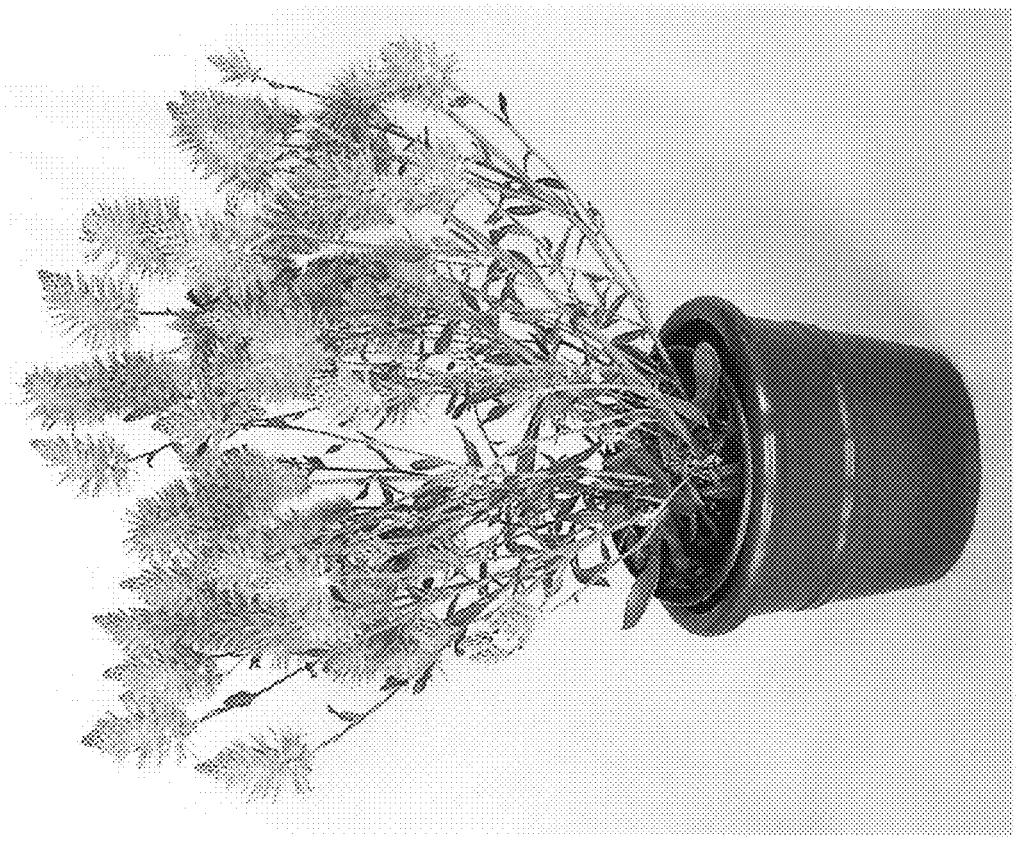

* * * * *